United States Patent [19]

Wilmot

[11] Patent Number: 5,713,866
[45] Date of Patent: Feb. 3, 1998

[54] NIPPLE PLUNGER

[75] Inventor: John Glyndwr Wilmot, Germantown, Md.

[73] Assignee: Meridian Medical Technologies, Inc., Columbia, Mass.

[21] Appl. No.: 548,762

[22] Filed: Oct. 26, 1995

Related U.S. Application Data

[63] Continuation of Ser. No. 280,884, Jul. 27, 1994, abandoned.

[51] Int. Cl.⁶ .................................................. A61M 5/20
[52] U.S. Cl. ...................... 604/139; 604/136; 604/135; 604/157
[58] Field of Search ..................... 604/157, 134, 604/135, 136, 139, 218; 433/90

[56] References Cited

U.S. PATENT DOCUMENTS

| | | |
|---|---|---|
| 2,186,711 | 1/1940 | Schleicher . |
| 2,887,108 | 5/1959 | Kendall . |
| 3,331,538 | 7/1967 | Higgins . |
| 3,368,557 | 2/1968 | Hassing et al. . |
| 3,413,974 | 12/1968 | Cohen . |
| 3,672,369 | 6/1972 | Brown . |
| 3,678,931 | 7/1972 | Cohen . |
| 3,738,539 | 6/1973 | Beich . |
| 3,825,003 | 7/1974 | Kruck . |
| 4,445,895 | 5/1984 | Marguilies . |
| 4,472,141 | 9/1984 | Dragan .................... 433/90 |
| 4,846,801 | 7/1989 | Okuda . |
| 5,007,904 | 4/1991 | Densmore et al. ........ 604/228 |
| 5,042,977 | 8/1991 | Bechtold et al. ......... 604/218 X |

(List continued on next page.)

FOREIGN PATENT DOCUMENTS

| | | |
|---|---|---|
| A-0 351 541 | 1/1990 | European Pat. Off. . |
| A-0 520 618 | 12/1992 | European Pat. Off. . |
| A-0 654 280 | 5/1995 | European Pat. Off. . |
| 1491696 | 5/1969 | Germany ................ 604/139 |
| 3914818 | 11/1990 | Germany ................ 604/157 |
| WO-A-91 10460 | 7/1991 | WIPO . |
| WO-A-92 09320 | 6/1992 | WIPO . |
| WO-A-95 21645 | 8/1995 | WIPO . |

*Primary Examiner*—Todd E. Manahan
*Attorney, Agent, or Firm*—Cushman, Darby & Cushman IP Group of Pillsbury Madison & Sutro LLP

[57] ABSTRACT

An automatic injector comprises a housing, a tubular cartridge disposed in the housing, the cartridge having a rearward portion thereof with a predetermined inner diameter and an inwardly extending shoulder connecting a forward portion of the cartridge with a smaller inner diameter than the predetermined diameter. A charge of liquid medicament is normally disposed in the cartridge, and a needle is disposed within the housing and adapted to communicate with the medicament through a forward end of the cartridge to dispense the medicament therethrough. A plunger disposed within the cartridge and rearwardly confines the medicament and has a rearward portion with a diameter sized to form a seal with the predetermined inner diameter of the rearward portion of the cartridge. The plunger is movable forwardly through the cartridge in slidingly sealed relation with respect thereto to displace the medicament through the needle. The plunger has a forward portion thereof being of a relatively reduced diameter than the rearward portion of the plunger and shaped i) to enter the forward portion of the cartridge to displace medicament therefrom through the needle and ii) to maintain fluid communication between the forward end of the cartridge through which the needle communicates with the medicament and a space within the cartridge between the plunger and the inwardly extending shoulder of the cartridge so as to dispense medicament from the cartridge until the plunger engages the shoulder and/or the forward end of the cartridge. A releasable energy source moves the plunger forwardly through the cartridge to dispense the medicament through the needle.

20 Claims, 3 Drawing Sheets

U.S. PATENT DOCUMENTS

| | | |
|---|---|---|
| 5,084,017 | 1/1992 | Maffetone . |
| 5,085,641 | 2/1992 | Sarnoff et al. . |
| 5,102,393 | 4/1992 | Sarnoff et al. .......................... 604/136 |
| 5,114,033 | 5/1992 | Golias et al. . |
| 5,137,516 | 8/1992 | Rand et al. ............................... 604/136 |
| 5,143,211 | 9/1992 | Miczka et al. . |
| 5,226,895 | 7/1993 | Harris . |
| 5,226,896 | 7/1993 | Harris . |
| 5,358,489 | 10/1994 | Wyrick ..................................... 604/136 |
| 5,514,097 | 5/1996 | Knauer ..................................... 604/136 |

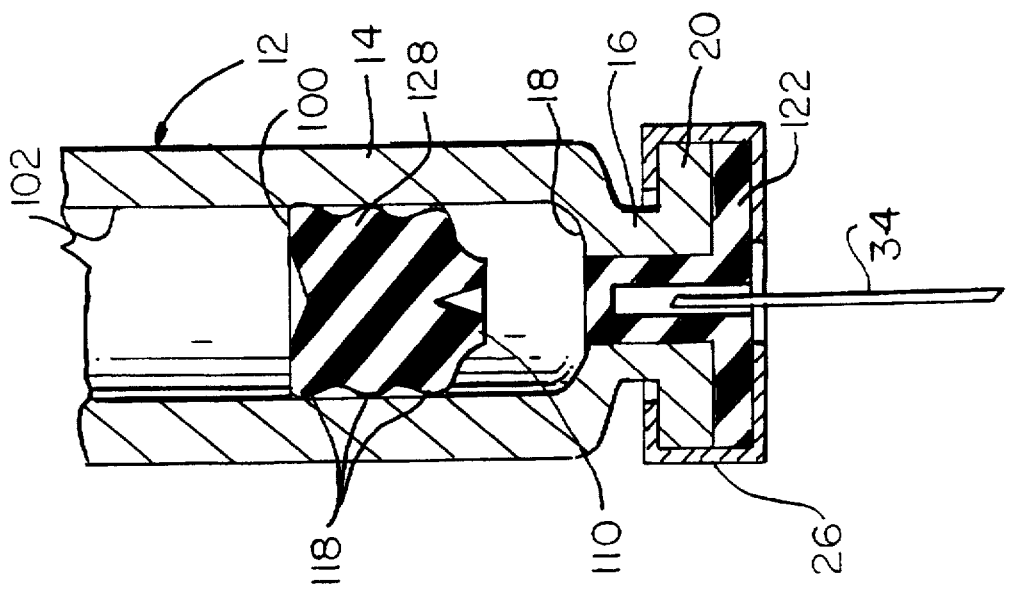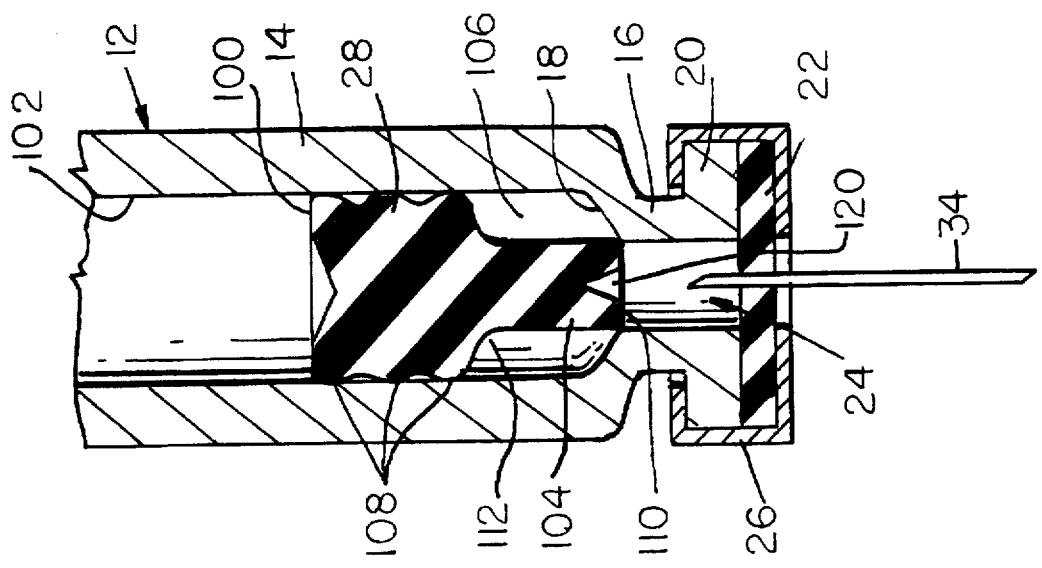

NIPPLE PLUNGER

This is a continuation of application Ser. No. 08/280,884, filed on Jul. 27, 1994, which was abandoned upon the filing hereof.

BACKGROUND OF THE INVENTION

This invention relates to medicament injection devices, and in particular, injection devices which are especially adapted to dispense substantially all of the medicament contained therein.

Injection devices, such as automatic injectors, are well known and are described, for example, in our previous U.S. Pat. Nos. 5,102,393 and 5,085,641, which are hereby incorporated by reference. Basically, an automatic injector is a device for enabling an individual to self-administer a dosage of a liquid medicament. An advantage of automatic injectors is that they contain a measured dosage of a liquid medicament in a sealed sterile condition capable of storage in such condition for extensive periods of non-use, during which period immediate injection of the stored dosage may be accomplished at any time. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's own tissue. Instead, an automatic injector includes a needle normally stored and concealed within a rigid outer housing. Also contained in the housing is a container or cartridge for containing the dose of medicament. A movable plunger rearwardly confines the medicament within the cartridge, and when a releasable spring assembly carried by the housing is released, the needle projects from a forward end of the housing, and the plunger is forced through the cartridge to displace the medicament therefrom through the needle and into the flesh of the user.

In such injectors, the medicament cartridge is normally made from a glass, metal or plastic material. There is normally a significant expense associated with manufacturing such cartridges, and as a result, the total cost of manufacturing the injector is increased. Therefore, in an attempt to reduce some of the manufacturing costs, some injectors have employed what is known as a "dental cartridge", which is a standard sleeve-like cartridge that is manufactured in bulk quantities for the medical industry. Dental cartridges are used in various applications as shown, for example, by U.S. Pat. Nos. 3,413,974; 3,368,557; 3,678,931; 3,825,003; 4,445,895; 5,226,895 and 5,226,896. Since such dental cartridges are mass produced, they are significantly less expensive than other types of cartridges, and it is thus desirable to incorporate them into automatic injectors. The use of dental cartridge shaped cartridges in automatic injectors is also advantageous since they can easily be filled with medicament by standard automatic filling machines.

A problem associated with the use of such dental cartridges, however, is that the forward portion thereof has a relatively reduced inner diameter relative to the rearward portion thereof. As a result, the plunger which travels forwardly through the cartridge is unable to fully dispense the portion of medicament which is disposed at the forwardmost portion in the cartridge. Thus, a small percentage of the medicament within the cartridge is effectively wasted. The expense associated with the wasted medicament is oftentimes very significant, especially when more costly medicaments such as human growth hormones are used.

To overcome this problem, there has been proposed an automatic injector having a plunger with a forward portion thereof shaped to enter the narrowed diameter portion of the cartridge to thereby displace the liquid medicament therefrom through the needle. However, heretofore such plungers have been ineffective in accomplishing their intended result. More particularly, plungers thus constructed have been unable to reach the forwardmost end of the cartridge, as liquid trapped between the plunger and an inwardly extending shoulder of the cartridge, which connects the forward and rearward portions of the cartridge, serves to hydraulically lock the piston in place a predetermined distance before reaching the forwardmost end of the cartridge, the limited biasing force of the spring assembly being insufficient to overcome such hydraulic lock.

It is thus an object of the present invention to solve the problems mentioned above. To accomplish this effect, the present invention provides an automatic injector comprising a housing having a tubular cartridge disposed therein. The cartridge has a rearward portion thereof with a predetermined inner diameter and an inwardly extending shoulder connecting the rearward portion of the cartridge to a forward portion of the cartridge. The forward portion of the cartridge has a relatively smaller inner diameter than the predetermined diameter of the rearward portion of the cartridge. A liquid medicament is normally disposed in the cartridge, and a needle disposed within the housing is adapted to communicate with the medicament through a forward end of the cartridge to dispense the medicament in response to a predetermined actuating procedure. A plunger disposed within the cartridge rearwardly confines the medicament therein. The plunger has a rearward portion with a diameter at least as great as the predetermined inner diameter of the rearward portion of the cartridge and is movable forwardly through the cartridge in slidingly sealed relation with respect thereto to displace the medicament through the needle. The plunger has a forward portion thereof which has a relatively reduced diameter as compared to the rearward portion of the plunger. The forward portion of the plunger is shaped (1) to enter the forward portion of the cartridge to displace medicament therefrom through the needle, and (2) to maintain fluid communication between the forward end of the cartridge through which the needle communicates with the medicament, and a space within the cartridge between the plunger and the inwardly extending shoulder of the cartridge so as to dispense medicament from the cartridge until the plunger engages either the shoulder or the forward end of the cartridge. A releasable energy source is constructed and arranged to move the plunger forwardly through the cartridge to dispense medicament through the needle in response to the predetermined actuating procedure.

It is also an object of the present invention to provide the plunger itself as described above to be used in conjunction with an automatic injector. While the present invention contemplates that the plunger can be used with a dental cartridge used in a manual injector (or syringe) it is understood that the plunger with dental cartridge of the present invention has special application in automatic injectors where hydraulic lock is more of a problem.

These and other objects of the present invention will become more apparent during the course of the following detailed description and appended claims. The invention may be best understood with reference to the accompanying drawings wherein illustrative embodiments are shown.

BRIEF DESCRIPTION OF THE DRAWINGS

FIG. 5 is a sectional view similar to FIG. 2, but showing a second embodiment of the present invention.

FIG. 6 is a sectional view similar to FIG. 2, but showing yet another embodiment of the present invention.

DETAILED DESCRIPTION OF THE PREFERRED EMBODIMENTS

Figure 1:
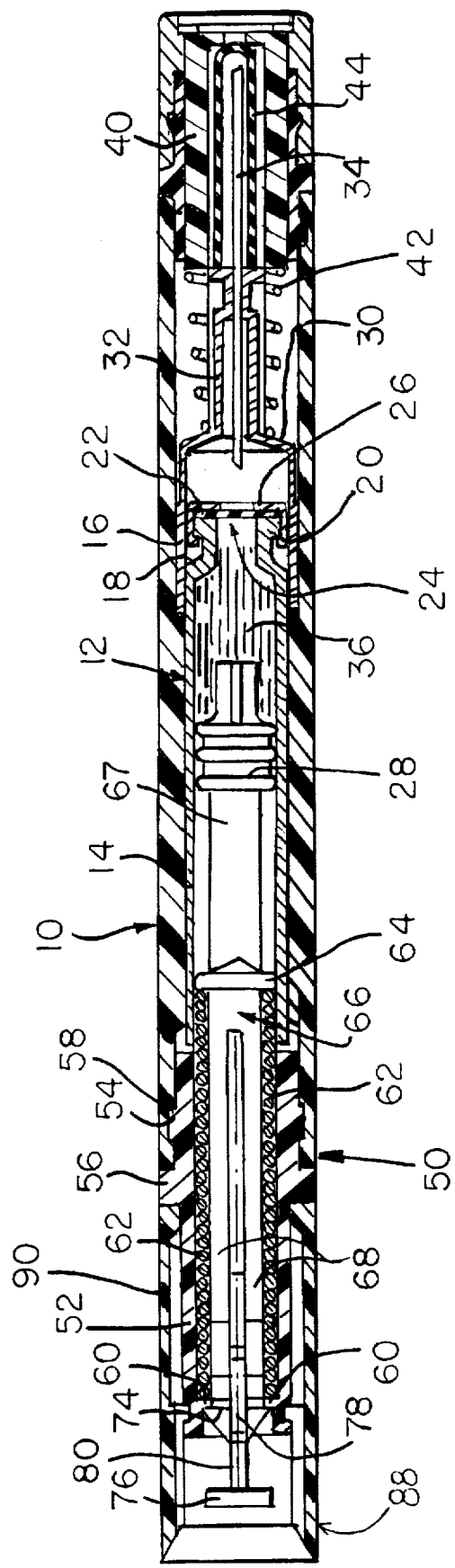
FIG. 1 is a longitudinal view, partly in section, of a first embodiment showing an automatic injector embodying the principles of the present invention.

FIG. 1 is a longitudinal view, partly in section, showing an embodiment of an automatic injector according to the present invention. It can be appreciated that the injector about to be described is merely illustrative in that the plunger of the present invention can be used in virtually any injection device which utilizes a medicament container having a necked down forward portion, often referred to in the art as a "dental cartridge." It can thus also be appreciated that the actuating procedure described herein with respect to the disclosed injector is also illustrative, and would differ according to the particular injection device used.

The injector of the present invention comprises a cylindrical outer housing or body 10. Disposed within the body 10 is a generally cylindrical medicament container in the form of a dental cartridge 12 which is open at its rearward end, and necked down at its forward end. The cartridge 12 is preferably made of glass, but can also be made of plastic or metal. The main portion 14 of the container or cartridge 12 extends rearwardly of the forward necked down forward portion 16 and has a predetermined inner diameter which is larger than the inner diameter of the necked down forward portion. These portions can be more clearly discerned in FIG. 2. The cartridge has an inwardly extending peripheral shoulder 18 which connects the main rearward portion of the cartridge with the smaller diameter forward portion of the cartridge. The forwardmost end (generally indicated at 24) of the cartridge has a radially outwardly extending flange 20 which receives a seal member 22 to close off the forward end. The seal member 22 is peripherally secured to the flange 20 at the forward end of the dental cartridge by means of an annular metallic clamping ring 26. A plunger 28 which is constructed in accordance with the principles of the present invention and described in greater detail later in the specification, closes the open rearward end of the cartridge 12 and is mounted therein for forward sliding movement in sealing relation with the interior surface thereof. Preferably the plunger is made of an elastic material such as rubber, but can also be made of a metal or plastic structure having an annular groove in which a resilient sealing "O" ring can be provided for sealing against the interior surface of the cartridge. This type of configuration is desirable, for example, in typical needle-less type injectors which require a substantial force to impact the rearward surface of the plunger to dispense medicament beneath the skin without a needle by virtue of the shear force of medicament escaping from the injector.

A slidable needle hub assembly 30 receives the forward end of the cartridge 12, including clamp ring 26, in sliding telescopic relation. The needle hub assembly 30 has a substantially narrowed diameter forward portion 32 thereof disposed in surrounding relation to a needle 34. The needle 34 is secured at a central peripheral portion thereof to the hub assembly 30. Forward movement of the cartridge 12 causes the rearward end of the needle to pierce the seal member 22 through the center of the annular clamp ring 26 to establish communication with a charge of medicament 36 contained in the cartridge through the forward end 24 of the cartridge during an injection operation.

A cover member 40 is disposed in surrounding relation to the forward portion of the needle and is spring biased by coil spring 42 to move forwardly in protective relation over the needle after an injection operation wherein the needle projects from the forward end of the device. A similar cover member and spring assembly is disclosed in U.S. Pat. No. 5,295,965, hereby incorporated by reference. Additionally, it can be appreciated that the forward portion of the needle may be covered by a protective sheath 44 to maintain the sterility of the needle and to act as a shock absorber for the cartridge as the cartridge is moved forwardly towards the front end of the body during an injection procedure. A similar sheath is disclosed in U.S. Pat. No. 3,882,863, hereby incorporated by reference.

A releasable spring assembly 50 includes a main rearward tubular housing member 52 having a forward annular ridge 54 formed on the exterior periphery thereof in rearwardly spaced relation to the forward end thereof and a rearward ridge 56 of slightly greater exterior diameter disposed in rearwardly spaced relation with respect to the forward ridge 54. The body 10 has the rearward interior periphery formed with an annular groove 58 so as to enable the rearward end portion of body 10 to be moved rearwardly over the forward end portion of the tubular housing member 52 of spring assembly 50 so as to be retained therein in a position in which the rearward extremity of the body 10 engages the forward surface of rearward annular ridge 56.

The tubular housing member 52 of spring assembly 50 is formed with an interior annular flange 60 spaced slightly inwardly from the rearward end thereof. The forward surface of the annular flange 60 is adapted to be engaged by a rearward volute of a coil spring 62 forming a part of the stressed spring assembly 50. Coil spring 62 operates as a releasable energy source for the injector of the present invention. It is understood that the present invention is not limited to the use of a coil spring and that any releasable energy source, such as an air spring, or chemical expansion reaction, may be used. The forward volute of the coil spring 62 engages a rearwardly facing surface of a forward flange 64 of a collet member, generally indicated at 66 (not shown in section). Optionally provided between the forward flange 64 of the collet and the plunger 28 is a spacer member 67. The spacer member permits the position of the plunger 28 within the cartridge to be controlled to determine the volume of the medicament chamber and thus the quantity of medicament carried in the chamber as disclosed in U.S. Pat. No. 4,031,893, hereby incorporated by reference. If the spacer is not provided, the collet may be extended so that the forward end thereof makes direct contact with the plunger.

The collet member 66 extends rearwardly from the forward flange 64 thereof within the coil spring 62. The rearward end portion of the collet member 66 is split so as to form a plurality (two) of rearwardly extending spring fingers 68. The rearward peripheral portion of the fingers 68 are formed with radially outwardly extending arcuate flanges presenting forwarding facing locking surfaces 74 which are adapted to engage along a generally radially extending plane with the rearwardly facing surface of the interior annular flange 60 of the housing member 52.

As shown, a safety actuating pin member, generally indicated at 76, is disposed in cooperating relation with the resilient fingers 68 in a storage position and includes a forward portion 78 which extends inwardly between the resilient fingers 68. The safety actuating member 76 also includes an intermediate portion 80 of a reduced diameter with respect to the forward portion 78, there being a frustoconical transition between the two portions. The larger forward portion 78 extending between fingers 68 prevents the fingers from moving radially inwardly toward one another, thereby maintaining the locking surfaces 74 of the spring fingers 68 in engagement with the rearwardly facing locking surfaces of flange 60. Thus, coil spring 62 is retained in a stressed condition between the forward flange 64 of the collet member 66 and the forwardly facing surface of the interior flange 60 of housing member 52.

As shown, cap structure 88 (not shown in section), when in its storage position, covers actuating member 76.

To effectuate an injection, the cap structure 88 is removed, and the user grasps body 10 in one hand and places the forward end of the injector against the portion of flesh to be injected. Next, the safety actuating pin member 76 is moved forwardly by a thumb or other finger so that the forward larger portion 78 of the actuating member 76 is moved into a position at which the interior portion of the fingers are shaped to more easily accommodate it. During such movement, the narrowed diameter intermediate portion is also moved into the fingers and permits the fingers to flex to an extent sufficient such that the locking surfaces 74 are moved off of the flange 60, allowing the collet member 66 to move forwardly under the action of the spring 62.

The collet 66 (and spacer 67 if provided) continues to move forwardly while the safety actuating pin member 76 is left behind in captured relation by the tubular housing member 52.

A more detailed description of the activating mechanism described above is provided in U.S. patent application Ser. No. 08/087,968, hereby incorporated by reference, which shows such mechanism used in a rectal administrator.

The collet member 66 or spacer 67 during its forward movement is forced against the rearward surface of plunger 28. This in turn causes the entire cartridge 12 to move forwardly within the body 10 so that the forward end of the needle 34 projects from the forward end of the injector (while compressing sheath 44 and spring 42) and the rearward end of the needle 22 to establish communication with the medicament through the forward end of the cartridge. Thereafter, the continued force of the collet member 66 and spacer 67 act to move the plunger 28 forwardly through the container 12. This movement of the plunger 28 pressurizes the liquid medicament 36 and begins to force it through the needle 34.

Figure 2:
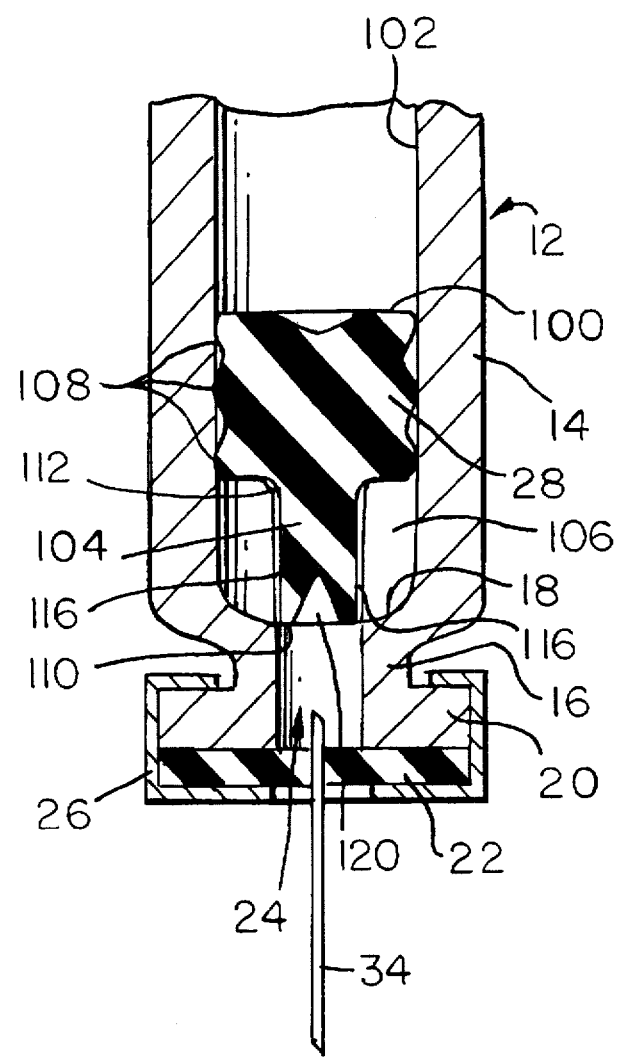
FIG. 2 is an enlarged longitudinal sectional view of a portion of the injector of FIG. 1, including a sectional view of the plunger of the present invention in an operative position.

In FIG. 2, it can be appreciated that the plunger 28 is made from an elastic material and has a rearward portion 100 with an outer diameter as defined by radial ridges 108 sized to form a seal with the inner surface 102 of the rearward portion 14 of the cartridge. Preferably, the rearward portion 100 of plunger 28 has a diameter which is slightly greater than the predetermined inner diameter of the rearward portion of the cartridge when the plunger is not peripherally compressed by the inner surface 102. This permits the plunger to move in slidingly sealed relation with respect to the inner surface of the rearward portion of the cartridge to displace the medicament through the needle 34. The plunger has a forward portion 104 thereof being of a relatively reduced diameter than the rearward portion 100. The forward portion 104 is shaped to enter the forward narrowed diameter portion 16 of the cartridge to displace medicament contained therein though the needle. It is preferable for the forward portion 104 to have a length substantially equal to the necked down forward portion 16 so that when it enters the forward portion 16, it comes into close proximity or, most preferably, into abutment with seal member 22 to substantially displace all of the medicament from the cartridge.

The forward portion 104 (or "nipple") is particularly shaped to maintain fluid communication between the space at the forward end (see, generally, numeral 24) of the cartridge where the rearward end of the needle communicates with the medicament and a space (see, generally, numeral 106) formed within the cartridge between the plunger 28 and the inwardly extending shoulder 18 of the cartridge. More specifically, the plunger 28 continues its forward movement within the cartridge until it is in close proximity with the forward narrowed diameter portion 16 of the cartridge. The forward portion 104 of the plunger is shaped so that when it enters the narrowed diameter forward portion 16 of the cartridge, it does not form a seal with respect thereto which cuts off fluid communication between the space at the forward end 24 of the cartridge through which the needle communicates (e.g., between plunger 28 and seal 22) and the space 106 between the shoulder 18 of the cartridge and the plunger 28.

In the prior art, the plungers which have been provided are problematic in that they are not particularly shaped to rid the medicament disposed in the narrowed diameter portion 16 of the cartridge. For example, while plungers have been provided which have a nipple that extends into the narrowed diameter portion, the nipple does not contact the forward seal to expel as much medicament as possible. In addition in the plungers which do provide an extended nipple, heretofore such plungers have been problematic in that the nipples thereof seal the space shown at the forward end 24 of the injector from the space 106 before the nipple is permitted to fully enter the forward portion of the cartridge and displace the medicament therefrom. The seal formed in such fashion causes the medicament contained in the space 106 to become trapped therein and act to hydraulically lock the plunger in place and prevent it from moving forwardly through the cartridge to the greatest extent possible, which extent would be such that the forwardmost surface 110 of the nipple engages the seal member 22, or such that an arcuate annular shoulder 112 forming a transitional portion of the plunger between the rearward portion 100 and nipple portion 104 engages the shoulder 18 of the cartridge.

Figure 3:
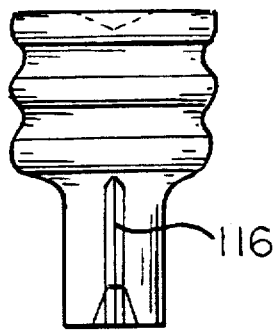
FIG. 3 is a perspective side view of the plunger of the present invention according to the first embodiment.

In the most preferred embodiment of the present invention, as shown in FIG. 2 and more clearly in FIG. 3, the forward portion 104 of the plunger accomplishes the intended function of allowing the plunger to move forwardly to the greatest extent possible by being provided with at least one axially extending groove 116 which permits the space at forward end 24 of the cartridge and the space 106 to communicate therethrough to prevent hydraulic lock. It is preferred that the at least one axially extending groove be disposed in an outer peripheral surface of the plunger.

While not shown, it can also be appreciated that the axially extending grooves can be provided as bores through more central portions of the forward reduced diameter portion of the plunger. For example, the bores could extend from forward surface 110 (see, FIG. 2) axially rearwardly through the nipple and then extend radially to exit at a more rearward portion of the plunger, e.g. at arcuate annular shoulder 112, so that the space at the forward end 24 and the space 106 can communicate.

In another embodiment, as shown in FIG. 5, it can be appreciated that the nipple portion of the plunger could simply have a sufficiently reduced outer diameter as compared to those known in the prior art to permit continuous communication between the two spaces until annular shoulder 112 of the plunger engages annular shoulder 18 of the cartridge, or until the forwardmost surface 110 of the plunger engages the seal 22 or rearward end of the needle 34. It such embodiment, it is preferred for the outer diameter of the nipple to be sufficiently reduced in size so that it does not make contact with the inner surface of the forward portion 16 of the cartridge.

Figure 4:
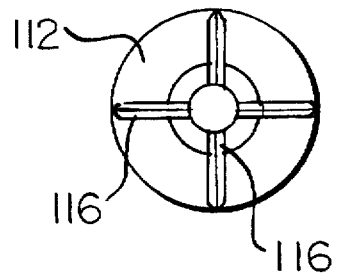
FIG. 4 is a perspective front view of the plunger of the present invention according to the first embodiment.

Referring back to the first embodiment, it is preferred that the peripheral grooves 116 extend substantially along the entire length of the nipple portion of the plunger. It may also be desirable to extend such peripheral grooves onto the annular shoulder portion 112 of the plunger 22, as shown in FIG. 4. Such grooves provided on the shoulder portion would extend substantially radially rather than axially. The grooves may also be provided in the forwardmost surface 110, as also shown in FIG. 4.

As shown in FIG. 2, it is also preferred that the nipple portion of the plunger be provided with a central bore 120 extending at least slightly into the forwardmost surface 110 so that the nipple can receive the rearward end of the needle when the nipple reaches its forwardmost point of travel (i.e., when it engages seal 22 or shoulder 18). This advantageously enables the plunger to travel completely through the cartridge without abutting the rearward end of the needle. Thus, the flow of medicament into the rearward end of the needle is maintained at all times.

In another embodiment shown in FIG. 6, it can be seen that the plunger 128 provided is shaped more like a conventional plunger in that the nipple portion thereof does not extend substantially into the necked down region of the cartridge.

In this embodiment, the seal 122 provided at the forward end of the cartridge has a "top-hat" configuration and extends substantially into the necked down region to prevent medicament from entering said region. As can be appreciated from FIG. 6, this configuration also prevents medicament from being wasted.

It thus will be seen that the objects of this invention have been fully and effectively accomplished. It will be realized, however, that the foregoing preferred specific embodiment has been shown and described for the purpose of this invention and it is subject to change without departure from such principles. Therefore, this invention includes all modifications encompassed within the spirit and scope of the following claims.

What is claimed is:

1. An automatic injector comprising:

a housing;

a tubular cartridge disposed in said housing, said cartridge having a rearward portion with a predetermined inner diameter and an inwardly extending shoulder connecting said rearward portion with a forward portion of said cartridge, said forward portion of the cartridge having a smaller inner diameter than said predetermined diameter;

a charge of liquid medicament normally disposed in said cartridge;

a forward seal normally forwardly confining the medicament within the cartridge;

a needle disposed within said housing and having a rearward end constructed and arranged to pierce said forward seal during actuation of said injector to enable said needle to establish communication with said medicament and dispense said medicament therethrough;

a movable plunger disposed within said cartridge and rearwardly confining said medicament in said cartridge, said plunger having a rearward portion with a diameter sized to form a rearward seal with said predetermined inner diameter of said rearward portion of the cartridge, said plunger being movable forwardly through said cartridge in slidingly sealed relation with respect thereto to displace the medicament through the needle during said actuation of said injector, said plunger having a forward portion thereof being of a relatively reduced diameter with respect to said rearward portion of the plunger, said forward portion of the plunger having a length substantially equal to a length of said forward portion of said cartridge, said forward portion of said plunger being shaped i) to enter a forward space defined by said forward portion of said cartridge to displace medicament therefrom through the needle and ii) to maintain fluid communication between the forward space defined by said forward portion of the cartridge and a peripheral space within said cartridge between said plunger and said inwardly extending shoulder of said cartridge so as to dispense medicament from said cartridge until the plunger engages at least one of said inwardly extending shoulder and said forward seal, said forward portion of said plunger having a recess therein constructed and arranged to receive said rearward end of said needle when said forward portion of said plunger enters said forward space defined by said forward portion of said cartridge; and a releasable energy source constructed and arranged to move said plunger forwardly through said cartridge to dispense said medicament through the needle in response to said actuation of the injector.

2. The injector according to claim 1, wherein the forward portion of the plunger has at least one axially extending groove disposed therein to permit medicament to travel therethrough from said peripheral space to said forward space until the plunger engages at least one of the shoulder and the forward seal.

3. The injector according to claim 2, wherein the plunger has an inwardly extending annular shoulder connecting said forward portion of the plunger with the rearward end of the plunger, said annular shoulder being constructed and arranged to engage the inwardly extending shoulder of the cartridge.

4. The injector according to claim 3, wherein the annular shoulder of the plunger has at least one radially extending groove disposed therein and intercommunicating with said at least one axially extending groove to permit the forward space in the cartridge and the peripheral space between the plunger and the inwardly extending shoulder of said cartridge to communicate therethrough until the annular shoulder of the plunger engages the inwardly extending shoulder of the cartridge.

5. The injector according to claim 4, wherein the radially and axially extending grooves are disposed in an outer peripheral surface of said plunger.

6. The injector according to claim 1, wherein said forward seal normally prevents communication between said medicament and said needle, said forward seal being conditionable to permit said needle to communicate with said medicament in response to said actuation of said injector.

7. The injector according to claim 6, further comprising an annular ring for fixing said forward seal to a forward end of said cartridge.

8. The injector according to claim 7, wherein a rearward end of said needle pierces said forward seal through an opening through said annular ring to establish said communication between said needle and said medicament in response to said actuation of said injector.

9. The injector according to claim 1, wherein said releasable energy source includes:
- a collet member movable forwardly through said housing to engage a rearward portion of said plunger to move said plunger through said cartridge in response to said actuation of said injector;
- a normally compressed coil spring releasable to move said collet member in response to said actuation of said injector; and
- a safety assembly constructed and arranged to maintain said spring compressed and said collet in an inoperative position prior to said predetermined actuating procedure.

10. The injector according to claim 1, wherein said forward portion of said plunger has said relatively reduced diameter thereof being sized such that it is sufficiently smaller than the inner diameter of the forward portion of said cartridge to enable said forward portion of the plunger to 1) enter said forward space defined by the forward portion of said cartridge to displace medicament therefrom though the needle and ii) to maintain fluid communication between the forward space in the cartridge and the peripheral space within said cartridge between said plunger and said inwardly extending shoulder of said cartridge so as to dispense medicament from said cartridge until the plunger engages at least one of said shoulder and said forward seal.

11. The injector according to claim 10, wherein the forward portion of the plunger has said diameter thereof sufficiently small such that it fails to make contact with a surface defining the inner diameter of the forward portion of the cartridge when said forward portion of the plunger enters said forward portion of the cartridge.

12. A plunger for use with a tubular cartridge containing a medicament capable of being dispensed from said cartridge, said cartridge having a rearward portion with a predetermined inner diameter and an inwardly extending shoulder connecting said rearward portion with a forward portion of the cartridge having a smaller inner diameter than said predetermined diameter, said plunger comprising:
- a rearward portion constructed and arranged to form a seal with said predetermined inner diameter of said rearward portion of the cartridge, said plunger being adapted to move forwardly through said cartridge in slidingly sealed relation with respect thereto,
- said plunger having a forward portion thereof being of a relatively reduced diameter with respect to said rearward portion of the plunger, said forward portion of the plunger having a length substantially equal to a length of said forward portion of said cartridge, said forward portion of said plunger being shaped i) to enter a forward space defined by said forward portion of said cartridge to displace medicament therefrom and ii) to maintain fluid communication between the forward space defined by the forward portion of the cartridge and a peripheral space within the cartridge between said plunger and said inwardly extending shoulder of the cartridge as said plunger moves forwardly within said cartridge and until the plunger engages at least one of the shoulder and a seal at the forward end of the cartridge,
- wherein the forward portion of the plunger has at least one axially extending groove disposed therein to permit the forward space and the peripheral space between the plunger and the inwardly extending shoulder of said cartridge to communicate therethrough until the plunger engages at least one of the shoulder and a seal disposed at the forward end of the cartridge,
- wherein the plunger has an inwardly extending annular shoulder connecting said forward portion of the plunger with the rearward end of the plunger, said annular shoulder being constructed and arranged to engage the shoulder of the cartridge, and
- wherein the annular shoulder of the plunger has at least one radially extending groove disposed therein and intercommunicating with said at least one axially extending groove to permit the forward end of the cartridge and the peripheral space between the plunger and the inwardly extending shoulder of said cartridge to communicate therethrough until the annular shoulder of the plunger engages at least one of the inwardly extending shoulder and the seal at the forward end of the cartridge.

13. The plunger according to claim 12, wherein the radially and axially extending grooves are disposed in an outer peripheral surface of said plunger.

14. The plunger according to claim 12, wherein said forward portion of said plunger has said relatively reduced diameter thereof being sized such that it is sufficiently smaller than the inner diameter of the forward portion of said cartridge to enable said forward portion of the plunger to 1) enter said forward portion of said cartridge to displace medicament therefrom and ii) to maintain fluid communication between the forward end of the cartridge and the space within said cartridge between said plunger and said inwardly extending shoulder of said cartridge so as to dispense medicament from said cartridge until the plunger engages at least one of said shoulder and a seal at the forward end of the cartridge.

15. The plunger according to claim 14, wherein the forward portion of the plunger has said diameter thereof sufficiently small such that it fails to make contact with a surface defining the inner diameter of the forward portion of the cartridge when said forward portion of the plunger enters said forward portion of the cartridge.

16. An automatic injector comprising:
- a housing;
- a tubular cartridge disposed in said housing, said cartridge having a rearward portion with a predetermined inner diameter and an inwardly extending shoulder connecting said rearward portion with a forward portion of said cartridge, said forward portion of the cartridge having a smaller inner diameter than said predetermined inner diameter of the rearward portion of the cartridge;
- a charge of liquid medicament normally disposed in said cartridge;
- a forward seal normally forwardly confining said medicament within said cartridge and having a portion thereof extending into said forward portion of the cartridge;
- a needle disposed within said housing and having a rearward end constructed and arranged to pierce said forward seal during actuation of said injector to enable said needle to establish communication with said medicament and dispense said medicament therethrough;
- a movable plunger disposed within said cartridge and rearwardly confining said medicament in said cartridge, said plunger having a diameter sized to form a rearward seal with said predetermined inner diameter of said rearward portion of the cartridge, said plunger being movable from a rearward position within said cartridge in which said plunger is separated from said forward seal so that said plunger and said forward seal define a space therebetween within which said medicament is normally disposed to a forward position within said cartridge in which said plunger and said forward seal are adjacent to one another and are cooperable so as to substantially displace the entirety of the space therebetween and thereby substantially displace the entirety of medicament through the needle, said forward portion of said plunger having a recess therein constructed and arranged to receive said rearward end of said needle when said forward portion of said plunger enters said forward space defined by said forward portion of said cartridge; and a releasable energy source constructed and arranged to move said plunger forwardly through said cartridge from said rearward position to said forward position to dispense said medicament through the needle in response to the actuation of the injector.

17. The automatic injector according to claim 16, wherein said forward seal has a top-hat configuration, and wherein a top portion of the top-hat configuration prevents said liquid medicament from entering said forward portion of said cartridge prior to said actuation.

18. The automatic injector according to claim 13, wherein said plunger and said forward seal are in contact with one another when said plunger is in said forward position.

19. A cartridge assembly for use in an injection device comprising:

a tubular cartridge having a rearward portion with a predetermined inner diameter and an inwardly extending shoulder connecting said rearward portion with a forward portion of said cartridge having a smaller inner diameter than said predetermined diameter;

a charge of liquid medicament disposed within said cartridge;

a forward seal forwardly confining said medicament within said cartridge, said forward seal capable of being broken to permit said medicament to exit said cartridge; and a plunger disposed within said cartridge and rearwardly confining said medicament in said cartridge, said plunger having a rearward portion with a diameter sized to form a rearward seal with said predetermined inner diameter of said rearward portion of the cartridge, said plunger being movable forwardly through said cartridge toward said forward seal to displace the medicament from the cartridge after said seal is broken, said plunger having a forward portion thereof being of a relatively reduced diameter than said rearward portion of the plunger and having a length substantially equal to a length of said forward portion of the cartridge, said forward portion of the plunger being shaped i) to enter said forward portion of said cartridge to displace medicament therefrom after said forward seal is broken, and ii) to maintain fluid communication between a space defined by the forward portion of the cartridge and a peripheral space within the cartridge between the plunger and the inwardly extending shoulder of the cartridge until the plunger engages at least one of the shoulder and the seal;

said forward portion of said plunger having a recess therein adapted to receive a rearward end of a needle which breaks said forward seal of said cartridge when said forward portion of said plunger enters said forward portion of said cartridge to displace medicament from the cartridge after said forward seal is broken.

20. An automatic injector comprising:

a housing;

a tubular cartridge disposed within said housing, said cartridge having a rearward portion with a predetermined inner diameter and an inwardly extending shoulder connecting said rearward portion with a forward portion of said cartridge, said forward portion of the cartridge having a smaller inner diameter than said predetermined inner diameter of the rearward portion of the cartridge;

a charge of liquid medicament disposed in said cartridge when said injector is in a storage condition;

a forward seal forwardly confining said medicament within said cartridge when said injector is in said storage condition;

a needle disposed within said housing and having a rearward end constructed and arranged to pierce said forward seal during actuation of said injector to enable said needle to establish communication with said medicament and dispense said medicament therethrough;

a movable plunger disposed within said cartridge and rearwardly confining said medicament in said cartridge, said plunger having a diameter sized to form a rearward seal with said predetermined inner diameter of said rearward portion of the cartridge, said plunger being movable from a rearward position within said cartridge in which said plunger is separated from said forward seal so that said plunger and said forward seal define a space therebetween within which said medicament is disposed when said injector is in said storage condition to a forward position within said cartridge in which said plunger and said forward seal are adjacent to one another and are cooperable so as to substantially displace the entirety of the space therebetween and thereby substantially displace the entirety of medicament through the needle in response to said predetermined actuating procedure, said forward portion of said plunger having a recess therein constructed and arranged to receive said rearward end of said needle when said forward portion of said plunger enters said forward space defined by said forward portion of said cartridge; and a releasable energy source constructed and arranged to move said plunger forwardly through said cartridge from said rearward position to said forward position to substantially dispense the entirety of said medicament through the needle in response to said actuation of the injector.

* * * * *